(12) United States Patent  
Vemulamada et al.

(10) Patent No.: US 11,590,290 B2  
(45) Date of Patent: Feb. 28, 2023

(54) DRUG DELIVERY SYSTEM

(71) Applicant: Robert Bosch GmbH, Stuttgart (DE)

(72) Inventors: Pardhasaradhi Vemulamada, Singapore (SG); Philipp Troebner, Frankfurt (DE); Soon Yee Chang, Singapore (SG); Claudia Kruse, Stuttgart (DE); Matthias Mahlich, Fellbach (DE); Suresh Palale, Singapore (SG)

(73) Assignee: Robert Bosch GmbH, Stuttgart (DE)

( * ) Notice: Subject to any disclaimer, the term of this patent is extended or adjusted under 35 U.S.C. 154(b) by 446 days.

(21) Appl. No.: 16/964,659

(22) PCT Filed: Feb. 21, 2019

(86) PCT No.: PCT/EP2019/054339  
§ 371 (c)(1),  
(2) Date: Jul. 24, 2020

(87) PCT Pub. No.: WO2019/170429  
PCT Pub. Date: Sep. 12, 2019

(65) Prior Publication Data  
US 2021/0052813 A1     Feb. 25, 2021

(30) Foreign Application Priority Data  
Mar. 8, 2018 (SG) ............................ 10201801940V

(51) Int. Cl.  
*G01R 33/31*     (2006.01)  
*A61M 5/315*     (2006.01)  
(Continued)

(52) U.S. Cl.  
CPC ........ *A61M 5/3155* (2013.01); *A61M 5/3158* (2013.01); *G01D 5/16* (2013.01);  
(Continued)

(58) Field of Classification Search  
CPC combination set(s) only.  
See application file for complete search history.

(56) References Cited

U.S. PATENT DOCUMENTS

| | | | |
|---|---|---|---|
| 5,929,631 A | 7/1999 | Striker et al. | |
| 9,784,802 B1 * | 10/2017 | Cox | ...................... G01R 33/096 |

(Continued)

FOREIGN PATENT DOCUMENTS

| | | |
|---|---|---|
| DE | 102006006784 A1 | 8/2007 |
| WO | 2016071912 A1 | 5/2016 |
| WO | 2016166338 A1 | 10/2016 |

OTHER PUBLICATIONS

International Search Report for PCT/EP2019/054339, dated Jun. 18, 2019.

(Continued)

*Primary Examiner* — Alvaro E Fortich  
(74) *Attorney, Agent, or Firm* — Norton Rose Fulbright US LLP; Gerard Messina

(57) ABSTRACT

A drug delivery system including: an oblong housing including a setting structure to set a dose of a drug via an angular position; and a sensor structure to determine the dose, including a magnet and a magnetic sensor, arranged so that at least one of an angular position and a displacement of the magnetic sensor relative to the magnet may be determined as a function of the electrical resistance of the magnetic sensor. The sensor structure is arranged in relation to the setting structure so that the angular position of the setting structure is determined as a function of the angular position and/or the displacement of the magnetic sensor. A sensor structure is also described including: a flexible foil, including a magnetic sensor, in a cylindrical shape configuration comprising an axis; and a magnet arranged at a line parallel to or collinear with the axis.

12 Claims, 3 Drawing Sheets

(51) Int. Cl.
*G01D 5/16* (2006.01)
*G01R 33/00* (2006.01)
*G01R 33/09* (2006.01)

(52) U.S. Cl.
CPC ....... *G01R 33/0094* (2013.01); *G01R 33/091* (2013.01); *G01R 33/093* (2013.01); *A61M 2205/3317* (2013.01); *A61M 2205/3592* (2013.01)

(56) References Cited

U.S. PATENT DOCUMENTS

| | | | |
|---|---|---|---|
| 2006/0161112 A1* | 7/2006 | Steffen | G01D 5/145 604/188 |
| 2007/0066940 A1 | 3/2007 | Karunaratne et al. | |
| 2010/0223797 A1* | 9/2010 | Peczalski | G01R 33/09 324/252 |
| 2013/0079727 A1* | 3/2013 | Schildt | A61M 5/24 604/207 |
| 2015/0160042 A1 | 6/2015 | Bogos et al. | |
| 2015/0290396 A1 | 10/2015 | Nagar et al. | |
| 2017/0286638 A1* | 10/2017 | Searle | G16H 40/63 |

OTHER PUBLICATIONS

Cubells-Beltran M.-D. et al., "Integration of GMR Sensors With Different Technologies," Sensors, Introduction, Section 4.1.1, vol. 16, No. 939, 2016, pp. 1-21.

* cited by examiner

DRUG DELIVERY SYSTEM

FIELD

The present invention relates to a drug delivery system comprising a sensor structure and to the sensor structure suitable for the drug delivery system.

BACKGROUND INFORMATION

Conventional drug delivery systems do not have a dose detection function. For example, the use of conventional insulin pens may require the user to manually record the dose for tracking the injections. A so-called "intelligent insulin pen" incorporates an additional adapter to be added as a cap over the pen. The module detects actuation of the device and the delivery event. Such systems include an optical motion detection system for detecting the actuation of the injection device or linear potentiometers for measuring position changes of a dose selector for determining the dose injected by a user. These systems are relatively bulky and costly.

SUMMARY

It is an object of the present invention to provide an improved drug delivery system for determining and tracking the dose, being less bulky, easier to manufacture and at a lower cost.

The present invention relates to a drug delivery system. In accordance with an example embodiment of the present invention, the drug delivery system may include an oblong housing. The oblong housing may include a setting structure configured to set a dose of a drug via an angular position. The drug delivery system may include a sensor structure. The sensor structure may be configured to determine the dose. The sensor structure may include a magnet and a magnetic sensor, arranged so that at least one of an angular position and a displacement of the magnetic sensor relative to the magnet may be determined as a function of the electrical resistance of the magnetic sensor. The magnet may be a permanent magnet. The sensor structure may be arranged in relation to the setting structure so that the angular position of the setting structure may be determined as a function of the angular position and/or the displacement of the magnetic sensor.

The present invention also relates to a sensor structure for determining axial and angular positions. In accordance with an example embodiment of the present invention, the sensor structure may include a flexible foil configured to be arranged in a cylindrical shape configuration comprising an axis. The sensor structure may include a magnet arranged at a line, which line may be parallel to or collinear with the axis. The flexible foil may include a magnetic sensor. The flexible foil and the magnet may be configured so that the magnet may be displaced, relative to the flexible foil in the cylindrical shape configuration, along the line.

BRIEF DESCRIPTION OF THE DRAWINGS

In the description below, various embodiments of the present invention are described with reference to figures.

DETAILED DESCRIPTION OF EXAMPLE EMBODIMENTS

Figure 1:
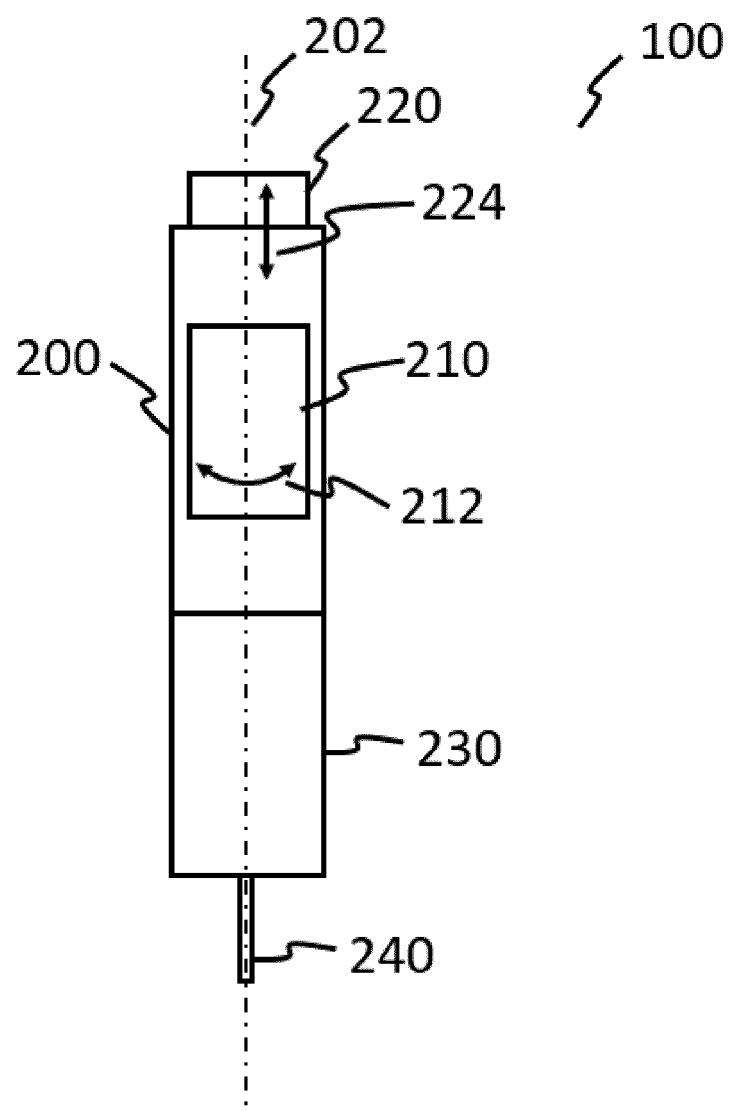
FIG. 1 is a schematic illustration of a drug delivery system 100 according to various embodiments of the present invention.

The following detailed description describes specific details and embodiments in which the present invention may be practiced. These embodiments are described in sufficient detail to enable those skilled in the art to practice the present invention. Other embodiments may be utilized and changes may be made without departing from the scope of the present invention. The various embodiments are not necessarily mutually exclusive, as some embodiments can be combined with one or more other embodiments to form new embodiments.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

The present invention illustratively described herein may suitably be practiced in the absence of any element or elements, limitation or limitations, not specifically disclosed herein. Thus, for example, the terms "comprising", "including", "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present invention. Thus, it should be understood that although the present invention has been specifically disclosed by exemplary embodiments and optional features, modification and variation of the present inventions embodied herein disclosed may be resorted to by those skilled in the art, and that such modifications and variations are considered to be within the scope of the present invention.

The drug delivery system, according to various embodiments of the present invention, may include a reservoir or means for receiving a reservoir, e.g., a cartridge containing a drug to be delivered. The drug delivery system according to various embodiments may include an outlet for delivering the drug, for example from an inlet. The inlet may, for example, be couplet to the cartridge (if available).

The drug delivery system, according to various embodiments of the present invention, may include an expelling mechanism, configured to release the dose of drug, for example through the outlet.

The oblong housing, according to various embodiments of the present invention, may include an actuator, for example a dosing button, configured to drive the expelling mechanism to release the dose of drug. According to various embodiments, at least part of the actuator displacement is axial. The term "axial" may mean, within the context of the present disclosure, along the elongation of the oblong housing or parallel thereto.

Within the scope of the present invention, and according to various embodiments of the present invention, a change in position between the magnet and the magnetic sensor refers to a relative change in position to each other. At least one of the magnet and the magnetic sensor may serve as reference and may be attached to a fixed position of a setting structure and/or housing so that the dose may be determined. The other of the magnet and the magnetic sensor may be attached to the setting structure so that the relative position or a relative change in position between the magnet and the magnetic sensor may be used to determine the dose. In various embodiments, the magnetic sensor may be an array of sensors. Within the scope of the present disclosure, and according to various embodiments of the present invention, the term "displacement" may refer to a change in position along the longest dimension or axis of the oblong housing. Within the scope of the present invention, and according to various embodiments of the present invention, the term "angular position" may refer to an angular position at a cross sectional plane of the oblong housing, wherein the cross sectional plane is substantially orthogonal to the longest dimension or axis of the oblong housing. Thus the "angular position" may also be called "cross sectional angular position" or "radial angular position". The angular position may mean the angle formed by rotating a magnet around the sensor from a pre-defined angle, which pre-defined angle may be a previously determined angle or an origin angle, e.g., the origin angle may correspond to a pre-determined dose, for example 0 mL, wherein the angle is in plane with the cross sectional plane. In various embodiments, the magnet needs to be arranged in such a position that, a magnetic field or a change in the magnetic field of the magnet, at the position of the sensor, may be detected by the sensor. For example, if the sensor has a preferred sensing axis to which the magnetic field should be parallel to obtain the strongest signal, then the magnet should be arranged so that at least a component of the magnetic field is substantially parallel to the sensing axis. The skilled person in the art may understand from the present disclosure that instead of arranged on the axis, the magnet and the magnetic sensor may be both arranged off axis, and the determination of the angle may require respective mathematical adjustments.

The present invention allows for the fabrication of a sensor structure using electronics based on polymeric materials used to detect the magnetic field change, for example, based on the position change upon the change of a dosage selector or dosing button. The sensor structure may have reduced cost and more environmentally friendly production because of the implementation of polymer electronics technology with reduced processing steps.

FIG. 1 is a schematic illustration of a drug delivery system 100 according to various embodiments of the present invention. The drug delivery system 100 may include an oblong housing 200. As shown in FIG. 1, by way of illustration, the housing 200 is oblong in the vertical direction. An oblong housing may, e.g. facilitate gripping the housing with hand for drug application. The housing 200 may include a setting structure 210, for example, a dose selector, and the setting structure 210 may be configured to set a dose of a drug via an angular position 212. For example, the setting structure 210 may be rotated by a user about a housing axis, relative to a fixed portion of the housing until the desired angular position is selected, as illustrated by way of example in FIG. 1 wherein an upper part of the housing may be rotated about the axis 202 relative to a fixed part of the housing 230. The setting structure 210 may further include indicia for indicating the selected dose (e.g. 1 mL, 1.5 mL, 2 mL). The drug delivery system 100 may comprise a sensor structure 300. The sensor structure 300 may comprise a magnet 310 and a magnetic sensor 320. The magnet 310 and the magnetic sensor 320 are arranged so that an angular position or a displacement of the magnetic sensor relative to the magnet may be determined as a function of the electrical resistance of the magnetic sensor.

In various embodiments of the present invention, the setting structure may include two parts movable relative to each other. The two parts may be rotatable and/or are linearly movable. The rotation may be, for example, to enable adjustment of an angular position by rotation about an axis. The linear movement may be, for example, to enable displacement in direction of the axis. One of the two parts may be non-movable relative to the housing, and may, e.g., be part of the housing, e.g., of an external part of the housing. The other part of the two parts may be movable relative to the housing, for example arranged on a component, e.g., partially enveloped by the housing, which may be moved relative to the housing by a user. One of the two parts may include the magnet and the other of the two parts may include the magnetic sensor. The two parts may be made of plastic.

In various embodiments of the present invention, the magnet may be arranged, e.g., attached to, the dosing button.

In various embodiments of the present invention, the magnetic sensor may be arranged, e.g., wrapped inside, the housing.

In various embodiments of the present invention, the drug delivery system 100 may include the sensor structure 300 and the setting structure 210, the sensor structure 300 may be arranged in relation to the setting structure 210 so that the angular position 212 of the setting structure 210 may be determined as a function of the angular position and/or the displacement of the magnetic sensor.

In various embodiments of the present invention, the term "magnetic sensor" may include one, two, three or more sensors, or an array of sensors.

In various embodiments of the present invention, the term "array of sensors" may mean 3, or more, preferably 4 or more sensors in a systematic arrangement, e.g., in rows and columns.

In various embodiments of the present invention, the term "sensor" or "sensors", without being preceded by magnetic may mean a sensor which may be used to measure a magnetic field, e.g., a transducer that varies a physical property other than magnetic field in response to a magnetic field. For example, a magneto-resistive sensor is a transducer that varies a resistance (the magneto resistance) in response to a magnetic field. For example, a GMR sensor is a transducer that varies an electrical resistance (the giant magneto resistance) in response to a magnetic field. GMR stands for Giant Magneto Resistance.

Figure 2:
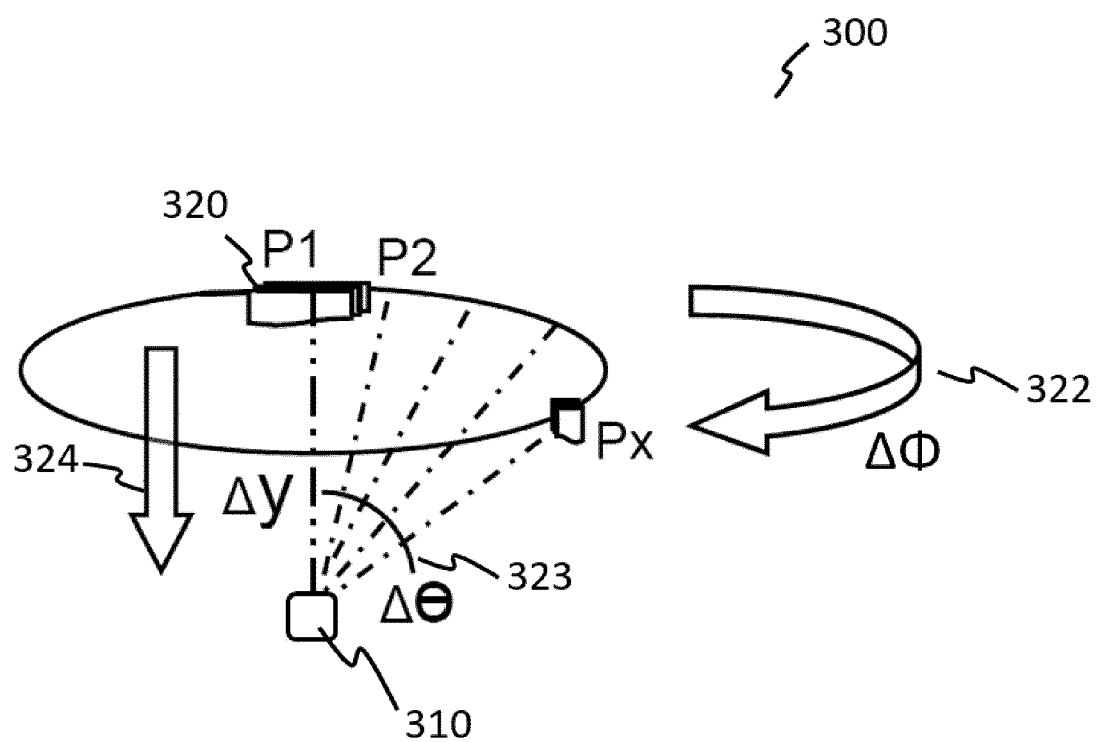
FIG. 2 is a schematic illustration of a sensor structure 300 according to various embodiments of the present invention.

FIG. 2 shows in more details the arrangement between the magnet and the magnetic sensor according to various embodiments. FIG. 2 shows schematically a magnet 310 and a magnetic sensor 320. The magnetic sensor may be moved on a circumference or arc thereof, e.g., in a direction 322 and displaced by an angle $\Delta\Phi$, for example, to an angular position P1, P2 or Px. The magnet may be arranged at an axis or parallel to an axis of the circumference or arc thereof. The magnet 310's axial position $\Delta y$, relative to the magnetic sensor 320's circumference plane may be varied, e.g. along direction 324. Since the movement is relative, the magnetic sensor may be moved instead of the magnet. Also, magnet and magnetic sensor may be exchanged in position, as long as the relative movements may be performed.

In various embodiments of the present invention, the relative movements of the magnet and the magnetic sensor may be constrained to the axial movement and angular movement, wherein the angular movement may be further restricted to the 322 direction.

In various embodiments of the present invention, the angle $\Delta\Phi$ may be determined when the axial position $\Delta y$ is at a known position, for example a rest position.

In some embodiments of the present invention, the angular position of the magnetic sensor relative to the magnet may be determined, e.g., as a function of the electrical resistance of the magnetic sensor. And because the sensor structure may be arranged in relation to the setting structure, the angular position of the setting structure may be determined, e.g., as being equal to the angular position of the magnetic sensor, or e.g., shifted therefrom by a constant angle. The angular position of the setting structure, on its turn, may be used to determine the selected dose.

In some embodiments of the present invention, the displacement of the magnetic sensor relative to the magnet may be determined, e.g., as a function of the electrical resistance of the magnetic sensor. And because the sensor structure may be arranged in relation to the setting structure, the displacement of the setting structure may be determined, e.g., as being equal to the displacement of the magnetic sensor, or, e.g., shifted therefrom by a constant distance. The axial position of the setting structure, on its turn, may be used to determine the selected dose. The pattern of the change in displacement may be used to determine the trigger for, or the dispensing, of the dose, for example a push on the actuator may correspond to a quick change in displacement.

Transients of the magnetic field, and consequently of the resistance of the magnetic sensor may be used to identify the trigger, i.e., the application of a dose, wherein slower changes, usually in a single direction over a certain period of time, can be used to determine the angular position of the magnetic sensor relative to the magnet and thus determine the selected dose.

Figures 3A, 3B:
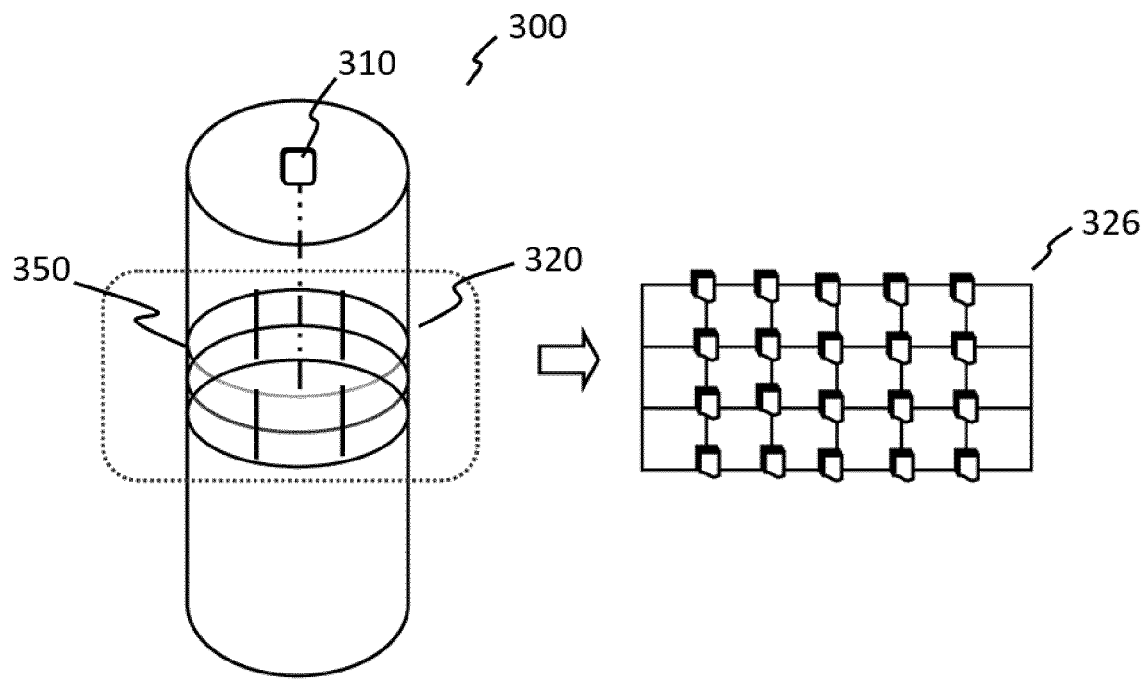
FIG. 3A is another schematic illustration of a sensor structure 300 wrapped onto a cylindrical section of the drug delivery system, according to some embodiments of the present invention.
FIG. 3B is a schematic illustration of an array 326 which may be arranged on for example a flexible foil 350 wrapped onto the cylindrical section, in accordance with an example embodiment of the present invention.

FIG. 3A shows a schematic of a sensor structure 300 including a magnet 310, a magnetic sensor 320 including an array of sensors 326 (illustrated in more detail in FIG. 3B). Each magnetic sensor of the array of sensors 326 may be, e.g., a GMR sensor.

By using an array of sensors, the axial displacement and angular position can be determined independently. For example, the array of sensors may be arranged in cylindrical configuration and a magnet arranged outside of the array of the cylindrical configuration. According to the determination of the position of the magnetic sensor within the array with most intense reading (e.g., GMR sensor with highest magneto resistance) it is possible to determine the displacement and angular position of the array of sensors at the same time. Further precision in displacement angular position may be obtained by considering more than one magnetic sensor, e.g. measuring the resistance of more than one GMR sensor of the array of sensors. The displacement and/or angular position may be calculated, for example by interpolation.

In some embodiments of the present invention, the array of sensors may extend at least in two dimensions, for example, if the array of sensors is wrapped to conform to the housing (e.g. wrapped in a cylindrical shape), the magnetic sensors may be arranged at certain, e.g. regular, angles, and certain, e.g. regular, axial (or parallel to the axis) distances.

In some embodiments of the present invention, the array of sensors may include, for example, 4 or more GMR sensors.

An array of sensors, according to the present disclosure, provides the advantage that magnetic sensors may be used which have no magnetic compass function, for example magneto-resistive sensors, such as GMR sensors. These sensors may be produced as a stack of layers with multiple layers, and may also be flexible.

In various embodiments of the present invention, the magnetic sensor may be arranged on a flexible foil 350. For example, the magnetic sensor, for example the array of sensors 326, is arranged or fabricated on a flexible foil 350, thus providing reduced size and weight.

In various embodiments of the present invention, the flexible foil may include a circuit for signal processing.

In various embodiments of the present invention, the flexible foil may include a circuit for wireless communication.

Figure 4:
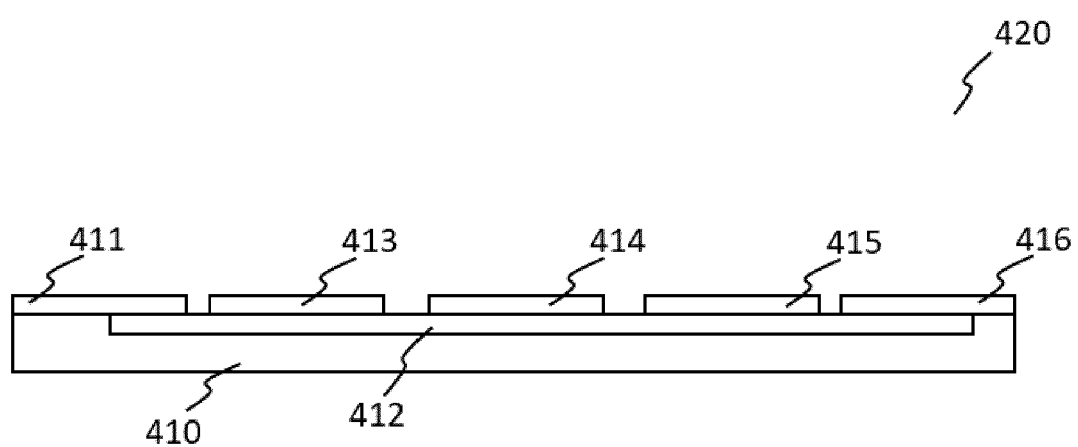
FIG. 4 is a schematic illustration of a section of a sensor structure 420, in a side view, according to various embodiments of the present invention.

FIG. 4 is a schematic illustration of a section of a sensor structure 420, in a side view, according to various embodiments. One section is shown for illustration purposes, as the sensor structure may include a plurality of such sections, for example on the same flexible substrate. The flexible substrate may be longer than the section shown in FIG. 4. The section of the sensor structure 420 may include a flexible substrate 410.

In various embodiments of the present invention, and as illustrated in FIG. 4, the section of the sensor structure 420 may include, e.g. on the flexible substrate 410, a magnetic sensor 413. The section of the sensor structure 420 may include, e.g. on the flexible substrate 410, a signal processing circuit 414. The section of the sensor structure 420 may include, e.g. on the flexible substrate 410, a communication and/or computational circuit 415.

In various embodiments of the present invention, the angular or axial position may be determined from a magnetic field property from the magnet, e.g. the magnitude of the magnetic field or the signal of the magnetic field. The magnetic field property, may be determined by the (i) signal processing circuit, by the (ii) communication and/or computational circuit, or by both, from the measurement of the magnetic sensor, e.g. from the resistance of a GMR sensor. The signal processing circuit, and the communication and/or computational circuit may be configured accordingly.

The magnetic sensor signal processing may be carried out on the foil by heterogeneous integration of Si based electronics, e.g. the combination of a flexible foil based substrate material with, e.g., printed conductive interconnection lines and the sensor elements and the assembly of standard surface mountable electronic components.

In various embodiments, and as illustrated in FIG. 4, the section of the sensor structure 420 may include, e.g., on the flexible substrate 410, an electrical interconnect layer 412 configured to provide the electrical coupling between the circuits and/or magnetic sensor. The interconnect layer 412 facilitates the electrical connections between the components on the flexible substrate, for example between any two or more of: the signal processing circuit 414, the communication and/or computational circuit 415, the interface 416, and the magnetic sensor 413.

In some embodiments of the present invention, the magnetic sensor may include a plurality of sensors and corresponding circuits for each sensor, e.g. one or all selected from: a signal processing circuit, a communication and/or computational circuit, an interface.

In some embodiments of the present invention, the sensor structure may include one circuit and/or interface for at least two, or all, sensors of the sensor structure. For example the sensor structure may include 2 or more sensors and a common interface. In another example the sensor structure may include 2 or more sensors and one communication and/or computational circuit, and one interface, in common for the 2 or more sensors, wherein for each sensor, the sensor structure may include a corresponding signal processing circuit, or may include a common signal processing circuit for the at least 2 sensors. The plurality of sensors, e.g., 3, 4, or more, may form an array of sensors. The plurality of sensors, e.g., in an array, may achieve improved detection resolution.

In various embodiments of the present invention, and as illustrated in FIG. 4, the section of the sensor structure 420 may include, for example on the flexible substrate 410, electrical contacts 411 configured for providing electrical coupling from at least one of the electrical interconnect layer 412, the circuits 414 or 415, and the sensor(s) 413 of the section of the sensor structure to an additional section of the sensor structure and/or to outside of the sensor structure, for example to electrical components external to the sensor structure and/or external to the drug delivery system. The sensor structure 420 may be powered, via electrical contacts 411, e.g. by a printed battery.

In various embodiments of the present invention, and as illustrated in FIG. 4, the section of the sensor structure 400 may include, an interface 416 to communicate data, e.g. data carrying an information of the current (e.g., magnitude of the current). The interface may include or be in electrical and signal communication to a near field communication device.

In various embodiments of the present invention, the electrical interconnect layer 412 may provide for electrical interconnection, e.g., for power and/or signal, between the magnetic sensor 413 and the signal processing circuit 414; and/or between the signal processing circuit 414 and the computational circuit 415; and/or between the computational unit and the interface 416.

In various embodiments of the present invention, the sensor structure may be configured to wirelessly communicate data from the magnetic sensor. For example, an acquired and/or processed sensor data carrying an information of the angular or axial position may be wirelessly communicated, for example to a mobile phone.

In various embodiments of the present invention, at least one, preferably each, of the magnetic sensors may include a GMR sensor. The GMR sensor may include GMR effect films. GMR effect films are possible to be applied on a flexible substrate with technologies such as screen printing, spray coating, inkjet printing, bar coating, roll coating. Multiple sensors may also be prepared on the flexible substrate to improve magnetic sensing resolution.

In accordance with one example embodiment of the present invention, the GMR sensor may include 20 to 50 double layers of ferromagnetic and non-magnetic conductors. Such sensor has a sensitivity within the range of ±300 mTesla, and it is sensitive to in-plane magnetic field change.

The magnetic sensor signal may be processed and sent out by a micro-controller and a near field communication device, which both may also be arranged on the flexible foil. Due to the use of the flexible foil, and/or GMR effect films, it is possible to achieve enhanced mechanical flexibility and the foil-based magnetic sensor systems are able to be embedded where rigid circuit boards cannot fit, weight and size are reduced and resolution is enhanced.

The invention claimed is:

1. A drug delivery system, comprising:
an oblong housing including a setting structure configured to set a dose of a drug via an angular position; and
a sensor structure configured to determine the dose, the sensor structure including a magnet and a magnetic sensor, arranged so that at least one of an angular position and a displacement of the magnetic sensor, relative to the magnet, is determined as a function of an electrical resistance of the magnetic sensor, and wherein the sensor structure is arranged in relation to the setting structure so that the angular or axial position of the setting structure is determined as a function of the angular position and/or the displacement of the magnetic sensor.

2. The drug delivery system according to claim 1, wherein the oblong housing includes an actuator configured to drive an expelling mechanism, to release the dose of drug, wherein at least part of a actuator displacement of the actuator is axial.

3. The drug delivery system according to claim 2, wherein the sensor structure is configured to determine an actuation of the actuator, by determining an axial displacement of the magnetic sensor relative to the magnet.

4. The drug delivery system according to claim 2, wherein the oblong housing includes a cylindrical section with a cylindrical axis, the cylindrical section including the setting structure and the actuator, wherein the magnet is positioned on the actuator at a line, the line being parallel to or collinear with the axis, and the magnetic sensor s positioned radially around the cylindrical axis.

5. The drug delivery system according to claim 1, wherein the magnetic sensor includes a GMR sensor.

6. The drug delivery system according to claim 5, wherein the electrical resistance of the magnetic sensor is a giant magneto resistance of the GMR sensor.

7. The drug delivery system according to claim 1, wherein the magnetic sensor includes a flexible foil.

8. The drug delivery system according to claim 1, wherein the magnetic sensor includes an array of sensors.

9. The drug delivery system according to claim 7, wherein the flexible foil includes a circuit for signal processing.

10. The drug delivery system according to claim 7, wherein the flexible foil includes a circuit for wireless communication.

11. A sensor structure for determining axial and angular positions, the sensor structure comprising:
a flexible foil configured to be arranged in a cylindrical shape configuration having an axis; and
a magnet arranged at a line, the line being parallel to or collinear with the axis;
wherein the flexible foil includes a magnetic sensor, and wherein the flexible foil and the magnet are configured so that the magnet may be displaced, relative to the flexible foil in the cylindrical shape configuration, along the line.

12. The sensor structure according to claim 11, wherein the magnetic sensor includes an array of GMR sensors.

\* \* \* \* \*